(12) United States Patent
Pateras et al.

(10) Patent No.: US 8,162,911 B2
(45) Date of Patent: Apr. 24, 2012

(54) COMPACT FOLDED ABSORBENT ARTICLE

(75) Inventors: Carrie Nicole Pateras, Appleton, WI (US); Garry Roland Woltman, Appleton, WI (US); Marcille Faye Ruman, Oshkosh, WI (US); Angela Rae Heck, Appleton, WI (US); Karyn Clare Schroeder, Neenah, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 833 days.

(21) Appl. No.: 11/242,520

(22) Filed: Oct. 3, 2005

(65) Prior Publication Data

US 2007/0078425 A1   Apr. 5, 2007

(51) Int. Cl.
*A61F 13/15* (2006.01)
*A61F 13/20* (2006.01)

(52) U.S. Cl. ........ 604/385.02; 604/385.04; 604/385.201

(58) Field of Classification Search ............. 604/385.02, 604/385.01, 385.201, 385.04
See application file for complete search history.

(56) References Cited

U.S. PATENT DOCUMENTS

| | | |
|---|---|---|
| 2,693,439 A | 11/1954 | Blanchard et al. |
| 2,772,678 A | 12/1956 | Leupold |
| 3,667,458 A | 6/1972 | Krebs |
| 4,023,570 A | 5/1977 | Chinai et al. |
| 4,061,820 A | 12/1977 | Magid et al. |
| 4,195,634 A | 4/1980 | Disalvo et al. |
| 4,336,804 A | 6/1982 | Roeder |
| 4,337,772 A | 7/1982 | Roeder |
| 4,376,440 A | 3/1983 | Whitehead et al. |
| 4,475,913 A | 10/1984 | Hlaban |
| 4,556,146 A | 12/1985 | Swanson et al. |
| 4,631,062 A | 12/1986 | Lassen et al. |
| 4,753,645 A | 6/1988 | Johnson |
| 4,802,884 A | 2/1989 | Froidh et al. |
| 4,950,264 A | 8/1990 | Osborn, III |

(Continued)

FOREIGN PATENT DOCUMENTS

BE          884898 A       2/1981
(Continued)

OTHER PUBLICATIONS

Zander, Teresa and Tom Keenan, "Improved Feminine Care Articles," published at IP.com as Document 132508D, Dec. 19, 2005, available online at "http://www.priorartdatabase.com/IPCOM/000132508D", 4 pages.

*Primary Examiner* — Michele M Kidwell
(74) *Attorney, Agent, or Firm* — Randall W. Fieldhack

(57) ABSTRACT

A personal care article (20) has a longitudinal-direction (22), a relatively shorter, lateral cross-direction (24), a first end-section (72), a second end-section (72*a*), and an intermediate-section (76) which is contiguous with and interposed between the first end-section (72) and the second end-section (72*a*). The article includes a liquid permeable topsheet layer (26), and a backsheet layer (28) which is operatively connected to the topsheet layer (26). At least a portion of the first end-section (72) has been folded along or otherwise includes a first end-fold-region (58) which is substantially convex along a topsheet-side of the article (20). Additionally, the first end-fold-region (58) is substantially concave along a backsheet-side of the article. At least a portion of the second end-section (72*a*) has been folded along or otherwise includes a second end-fold-region (62) which is substantially convex along the topsheet-side of the article (20).

13 Claims, 10 Drawing Sheets

U.S. PATENT DOCUMENTS

| | | | |
|---|---|---|---|
| 4,959,265 | A | 9/1990 | Wood et al. |
| 5,011,480 | A | 4/1991 | Gossens et al. |
| 5,088,993 | A | 2/1992 | Gaur |
| 5,197,959 | A | 3/1993 | Buell |
| 5,221,276 | A | 6/1993 | Battrell |
| 5,387,450 | A | 2/1995 | Stewart |
| 5,453,296 | A | 9/1995 | Lauritzen et al. |
| 5,484,636 | A | 1/1996 | Berg, Jr. et al. |
| 5,569,228 | A * | 10/1996 | Byrd et al. ............... 604/385.02 |
| 5,591,153 | A | 1/1997 | Mattingly, III |
| 5,611,790 | A | 3/1997 | Osborn, III et al. |
| 5,662,758 | A | 9/1997 | Hamilton et al. |
| H1698 | H | 11/1997 | Lloyd et al. |
| 5,694,739 | A | 12/1997 | Mattingly, III |
| 5,769,837 | A * | 6/1998 | Parr .............................. 604/390 |
| 5,993,430 | A | 11/1999 | Gossens et al. |
| 6,004,308 | A | 12/1999 | Haddock |
| 6,168,582 | B1 | 1/2001 | Hasegawa |
| 6,176,850 | B1 | 1/2001 | Rosenfeld et al. |
| 6,186,993 | B1 | 2/2001 | Toyoshima et al. |
| 6,293,932 | B1 | 9/2001 | Balzar et al. |
| 6,394,990 | B1 | 5/2002 | Rosenfeld et al. |
| 6,436,080 | B1 | 8/2002 | Carlucci et al. |
| 6,565,549 | B1 | 5/2003 | Allen et al. |
| 6,572,600 | B1 | 6/2003 | Roe et al. |
| 6,575,947 | B1 | 6/2003 | Tameishi et al. |
| 6,695,827 | B2 | 2/2004 | Chen et al. |
| 2003/0014032 | A1 | 1/2003 | Kashiwagi et al. |
| 2004/0018365 | A1 | 1/2004 | Krautkramer et al. |
| 2004/0163179 | A1 | 8/2004 | Trefethren et al. |
| 2004/0167489 | A1* | 8/2004 | Kellenberger et al. ... 604/385.01 |
| 2004/0186448 | A1 | 9/2004 | Misek et al. |
| 2005/0085780 | A1 | 4/2005 | Corlett |
| 2005/0085781 | A1* | 4/2005 | Corlett ..................... 604/385.02 |
| 2005/0131371 | A1 | 6/2005 | Fell et al. |
| 2005/0182374 | A1 | 8/2005 | Zander et al. |
| 2005/0251101 | A1 | 11/2005 | Becker |

FOREIGN PATENT DOCUMENTS

| | | | |
|---|---|---|---|
| EP | 0 313 426 | A1 | 4/1989 |
| EP | 0 688 549 | A2 | 12/1995 |
| EP | 0 471 384 | B1 | 10/1996 |
| EP | 0 850 628 | A1 | 7/1998 |
| EP | 1 407 747 | A1 | 4/2004 |
| FR | 2 765 474 | A1 | 1/1999 |
| GB | 2 267 830 | A | 12/1993 |
| GB | 2 298 627 | A | 9/1996 |
| GB | 2 380 138 | A | 4/2003 |
| JP | 11-056901 | A | 3/1999 |
| JP | 2006-103689 | A | 4/2006 |
| WO | WO 92/04000 | A1 | 3/1992 |
| WO | WO 96/020668 | A1 | 7/1996 |
| WO | WO 99/055270 | A1 | 11/1999 |
| WO | WO 00/21477 | A1 | 4/2000 |
| WO | WO 2005/060894 | A1 | 7/2005 |

* cited by examiner

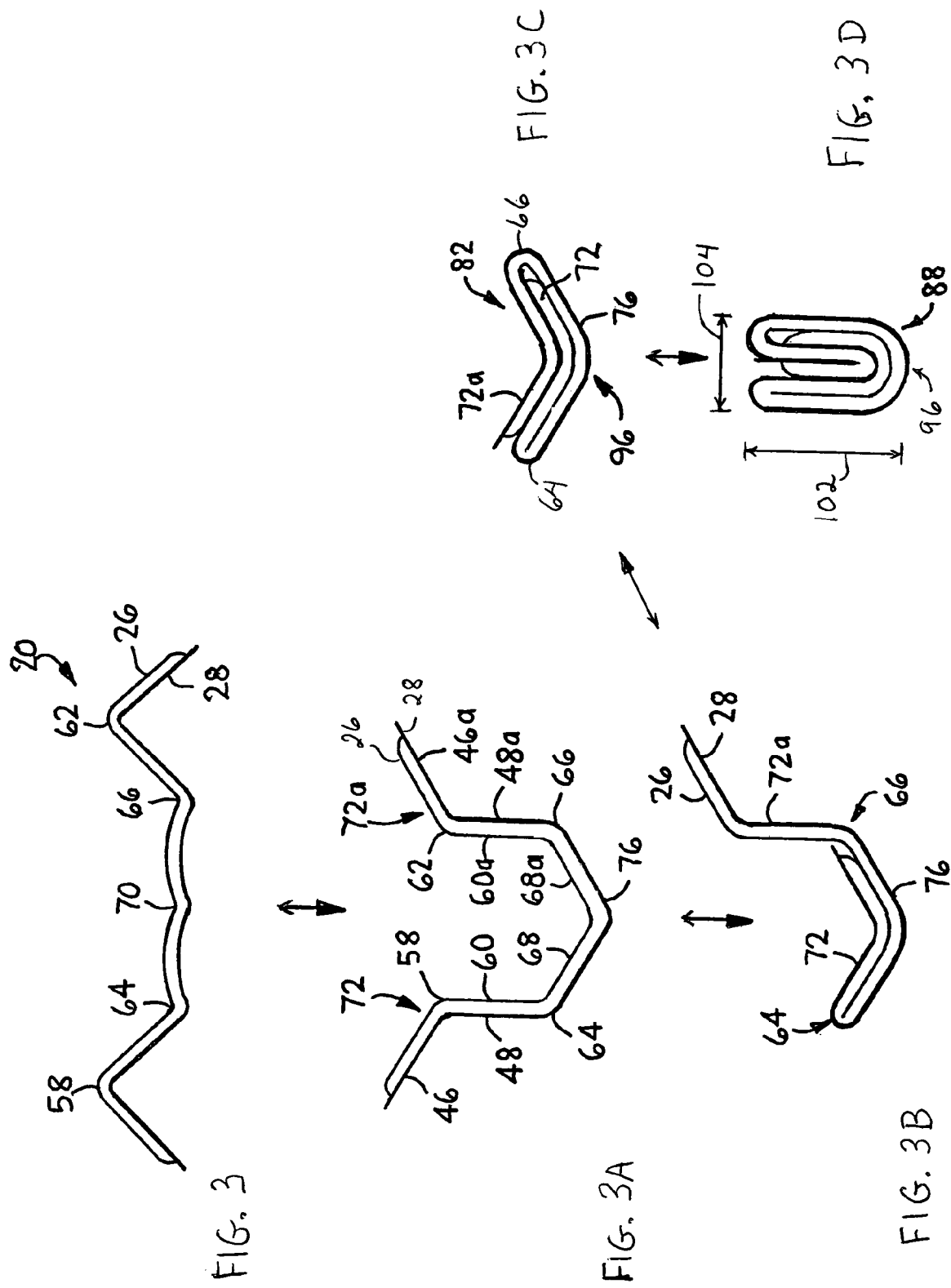

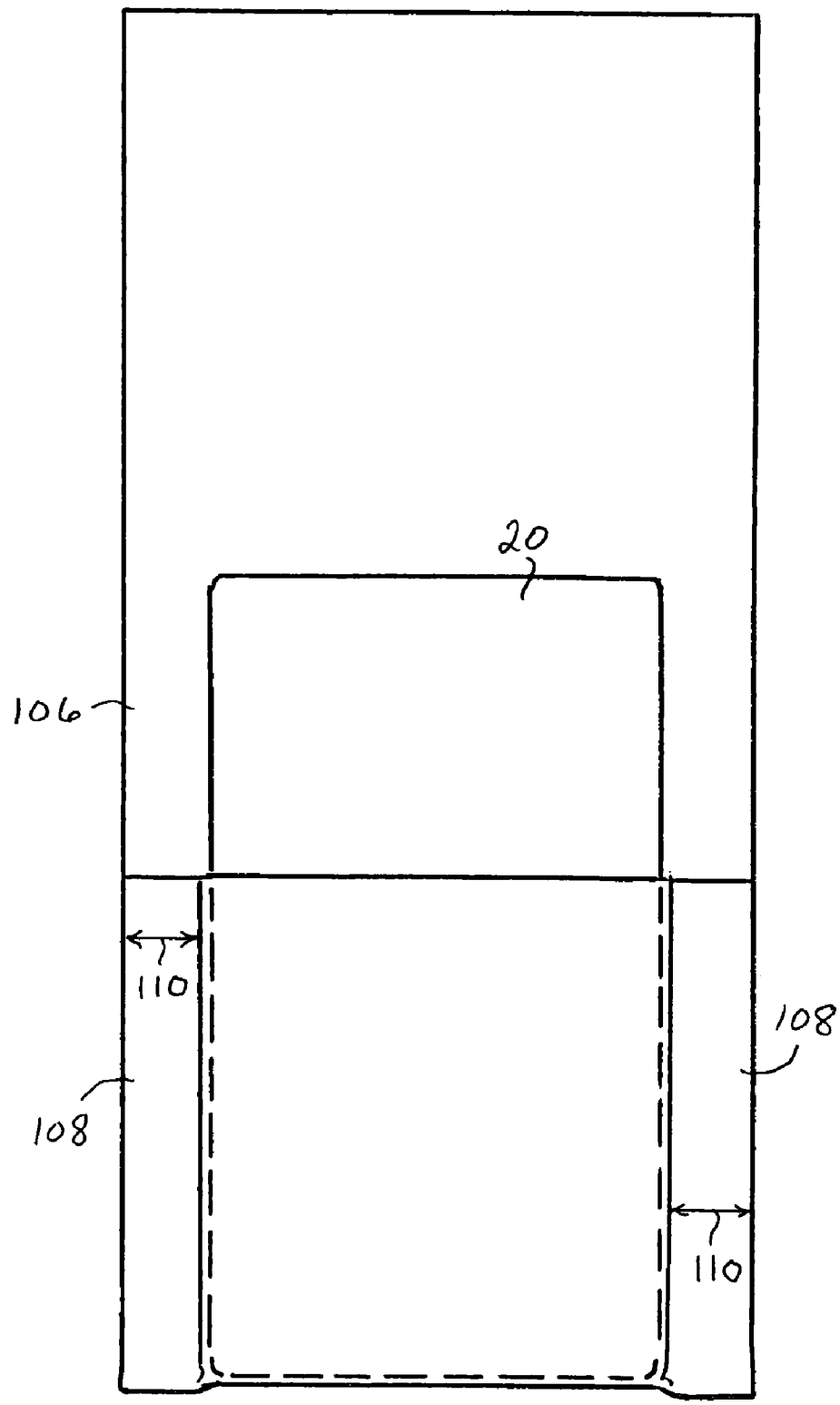

COMPACT FOLDED ABSORBENT ARTICLE

FIELD OF THE INVENTION

The present invention relates to a personal care article. More particularly, the present invention pertains to a personal care absorbent article, such as an absorbent feminine care or adult care pad. The personal care article can be operatively secured to a selected garment of a wearer.

BACKGROUND OF THE INVENTION

Absorbent products intended to absorb discharged body fluids are well known in the art. Such absorbent products generally comprise a fibrous mass or other absorbent body which can absorb and hold the body fluids. Similarly, it is well known that feminine care articles have been employed to absorb and hold liquids, such as urine and/or menses. The absorbent articles have included various systems of liquid-handling layers, such as intake layers, distribution layers, retention layers and the like. The absorbent products are worn against the body. To keep these products on the body, the products have included either a system of fasteners or a garment attachment system. For example, feminine care articles have employed a garment-attachment adhesive to help secure the article to a wearer's undergarment. Additionally, the absorbent articles have included wing portions which can help to hold the article in place at a selected location in the undergarment. Various fasteners have been employed to secure the wing portions in a desired configuration during ordinary use. The fasteners have included adhesive fasteners as well as mechanical fasteners, and the mechanical fasteners have included conventional, hook-and-loop fasteners. Individual absorbent articles have been folded or rolled to reduce the size of the article for storage and transport prior to use, and each article has been enclosed in a corresponding, individual storage pouch or other container.

The absorbent products undergo deformation during wear, and the deformation has caused the product to take undesired shapes or configurations. The product can fold and shift to expose the wearer or the wearer's clothing to undesired regions of the product. In particular situations, the deformation has caused the fasteners or garment attachment system to detach and come in contact with the wearer. The contact has caused excessive irritation and discomfort, particularly when a garment-attachment adhesive has contacted the wearer's skin or hair. The occurrences of the undesirable deformations and configurations increase when the absorbent article has been constructed with greater flexibility and thinness.

Conventional absorbent articles have been folded or rolled for placement in a storage pouch. Particular storage configurations, however, can increase the occurrences of the undesired deformations of the absorbent article. Additionally, the storage configurations have not provided desired combinations of small size, discretion, ease of use. As a result, there has been a continued need for improved absorbent articles that can be discreetly carried in a person's hand, provide desired levels of liquid intake and retention, provide a desired ease of securement to a wearer's undergarment, and provide desired levels of comfort to the wearer.

BRIEF DESCRIPTION OF THE INVENTION

Generally stated, the present invention provides an absorbent article having a longitudinal direction, a lateral direction, first and second longitudinally opposed end-sections, and an intermediate section located between the end portions. The article includes a liquid permeable topsheet layer, and a backsheet layer which is operatively connected to the topsheet layer. At least a portion of the first end-section has been folded along or otherwise includes a first end-fold-region which is substantially convex along a topsheet-side of the article. Additionally, the first end-fold-region is substantially concave along a backsheet-side of the article. At least a portion of the second end-section has been folded along or otherwise includes a second end-fold-region which is substantially convex along the topsheet-side of the article. Additionally, the second end-fold-region can be substantially concave along the backsheet-side of the article.

By incorporating its various features and configurations, the article of the invention can better provide desired combinations of small size, discretion, comfort and ease of use. The absorbent articles of the invention can, for example, be more discreetly carried in a person's hand, can provide desired levels of liquid intake and retention, and can provide a desired ease of securement to a wearer's undergarment. Where the article includes a garment-attachment mechanism (e.g. adhesive), for example, the configurations of the article can help avoid excessive skin irritation caused by the garment-attachment mechanism, and can help avoid undesired attachments of the garment-attachment mechanism to other portions of the article or to the body of a wearer.

BRIEF DESCRIPTION OF THE DRAWINGS

The various features, aspects and advantages of the present invention will become better understood with reference to the following description, appended claims and accompanying drawings where:

FIG. 3 shows a representative, side elevational view of an absorbent article that has been subjected to a composite folding operation.

FIG. 3A shows a representative, side elevational view of an absorbent article that is in a transitory position of a composite folding operation.

FIG. 3B shows a representative, side elevational view of an absorbent article that has been folded about a first supplemental-fold-region.

FIG. 3C shows a representative, side elevational view of an absorbent article that has been folded about a second supplemental-fold-region.

FIG. 3D shows a representative, side elevational view of an absorbent article that has been folded about a composite-fold-region.

FIG. 9A shows a representative arrangement of an absorbent article in an opened pouch or wrapper member.

DETAILED DESCRIPTION OF THE INVENTION

Figure 1:
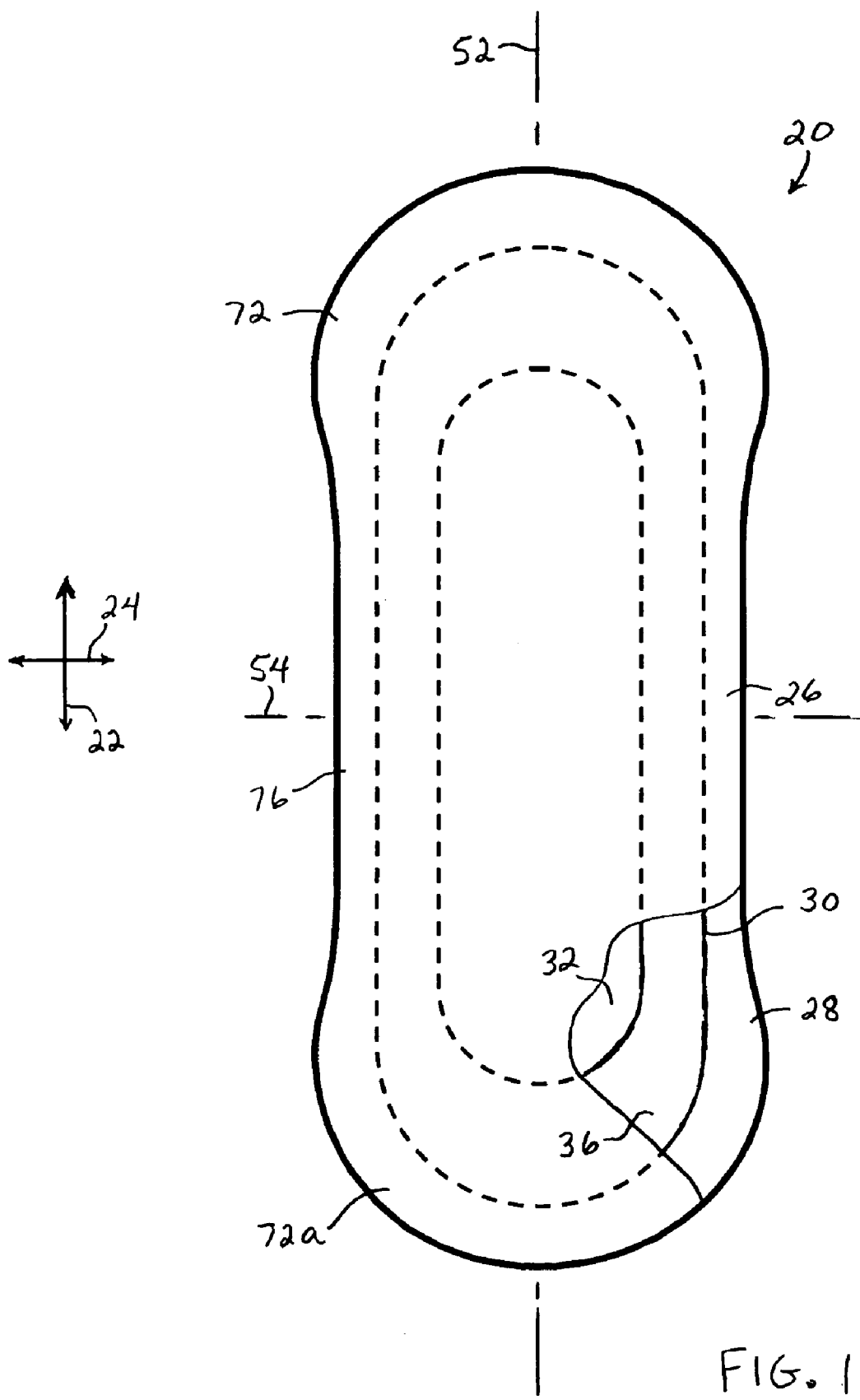
FIG. 1 shows a representative, partially cut-away, top, plan view of a bodyside of an absorbent article.

It should be noted that, when employed in the present disclosure, the terms "comprises", "comprising" and other derivatives from the root term "comprise" are intended to be open-ended terms that specify the presence of any stated features, elements, integers, steps, or components, and are not intended to preclude the presence or addition of one or more other features, elements, integers, steps, components, or groups thereof.

By the terms "particle," "particles," "particulate," "particulates" and the like, it is meant that the material is generally in the form of discrete units. The units can comprise granules, powders, spheres, pulverized materials or the like, as well as combinations thereof. The particles can have any desired shape such as, for example, cubic, rod-like, polyhedral, spherical or semi-spherical, rounded or semi-rounded, angular, irregular, etc. Shapes having a large greatest dimension/smallest dimension ratio, like needles, flakes and fibers, are also contemplated for inclusion herein. The terms "particle" or "particulate" may also include an agglomeration comprising more than one individual particle, particulate or the like. Additionally, a particle, particulate or any desired agglomeration thereof may be composed of more than one type of material.

As used herein, the term "nonwoven" refers to a fabric web that has a structure of individual fibers or filaments which are interlaid, but not in an identifiable repeating manner.

As used herein, the terms "spunbond" or "spunbonded fiber" refer to fibers which are formed by extruding filaments of molten thermoplastic material from a plurality of fine, usually circular, capillaries of a spinneret, and then rapidly reducing the diameter of the extruded filaments.

As used herein, the phrase "meltblown fibers" refers to fibers formed by extruding a molten thermoplastic material through a plurality of fine, usually circular, die capillaries as molten threads or filaments into a high velocity, usually heated, gas (e.g., air) stream which attenuates the filaments of molten thermoplastic material to reduce their diameter. Thereafter, the meltblown fibers are carried by the high velocity gas stream and are deposited on a collecting surface to form a web of randomly disbursed meltblown fibers.

"Coform" as used herein is intended to describe a blend of meltblown fibers and cellulose fibers that is formed by air forming a meltblown polymer material while simultaneously blowing air-suspended cellulose fibers into the stream of meltblown fibers. The meltblown fibers containing wood fibers are collected on a forming surface, such as provided by a foraminous belt. The forming surface may include a gas-pervious material, such as spunbonded fabric material, that has been placed onto the forming surface.

As used herein, the phrase "complex liquid" describes a liquid generally characterized as being a viscoelastic liquid comprising multiple components having inhomogeneous physical and/or chemical properties. It is the inhomogeneous properties of the multiple components that challenge the efficacy of an absorbent or adsorbent material in the handling of complex liquids. In contrast with complex liquids, simple liquids, such as, for example, urine, physiological saline, water and the like, are generally characterized as being relatively low-viscosity and comprising one or more components having homogeneous physical and/or chemical properties. As a result of having homogeneous properties, the one or more components of simple liquids behave substantially similarly during absorption or adsorption, although some components may be absorbed or adsorbed more readily than others.

Although a complex liquid is generally characterized herein as including specific components having inhomogeneous properties, each specific component of a complex liquid generally has homogeneous properties. Consider for example a representative complex body-liquid having three specific components: red blood cells, blood protein molecules and water molecules. Upon examination, one skilled in the art could easily distinguish between each of the three specific components according to their generally inhomogeneous properties. Moreover, when examining a particular specific component such as the red blood cell component, one skilled in the art could easily recognize the generally homogeneous properties of the red blood cells.

As used herein, the term "hydrophilic" describes fibers or the surfaces of fibers that are wetted by the aqueous liquids in contact with the fibers. The degree of wetting of the materials can, in turn, be described in terms of the contact angles and the surface tensions of the liquids and materials involved. Equipment and techniques suitable for measuring the wettability of particular fiber materials can be provided by a Cahn SFA-222 Surface Force Analyzer System, or a substantially equivalent system. When measured with this system, fibers having contact angles less than 90° are designated "wettable" or hydrophilic, while fibers having contact angles equal to or greater than to 90° are designated "nonwettable" or hydrophobic. When comparing materials, a material that forms a relatively larger contact angle with water is relatively less hydrophilic than a material that forms a smaller contact angle with water.

As used herein, the phrase "absorbent article" refers to devices which absorb and contain body liquids, and more specifically, refers to devices which are placed against or near the skin to absorb and contain the various liquids discharged from the body. The term "disposable" is used herein to describe absorbent articles that are not intended to be laundered or otherwise restored or reused as an absorbent article after a single use. Examples of such disposable absorbent articles include, but are not limited to: health care related products including surgical drapes, gowns, and sterile wraps; personal care absorbent products such as feminine hygiene products (e.g., sanitary napkins, pantiliners, tampons, interlabial devices and the like), infant diapers, children's training pants, adult incontinence products and the like; as well as absorbent wipes and covering mats.

Disposable absorbent articles such as, for example, many of the feminine care absorbent products, can include a liquid pervious topsheet, an operatively liquid-impervious backsheet joined to the topsheet, and an absorbent core positioned and held between the topsheet and the backsheet. The topsheet is operatively permeable to the liquids that are intended to be held or stored by the absorbent article, and the backsheet may be substantially impermeable or otherwise operatively impermeable to the intended liquids. The absorbent article may also include other components, such as liquid wicking layers, liquid intake layers, liquid distribution layers, transfer layers, barrier layers, and the like, as well as combinations thereof. Disposable absorbent articles and the components thereof can operate to provide a body-facing surface and a garment-facing surface. As used herein, the body-facing or bodyside surface means that surface of the article or component which is intended to be disposed toward or placed adjacent to the body of the wearer during ordinary use, while the outward, outward-facing or garment-side surface is on the opposite side, and is intended to be disposed to face away from the wearer's body during ordinary use. Such outward surface may be arranged to face toward or placed adjacent to the wearer's undergarments when the absorbent article is worn.

Figure 2:
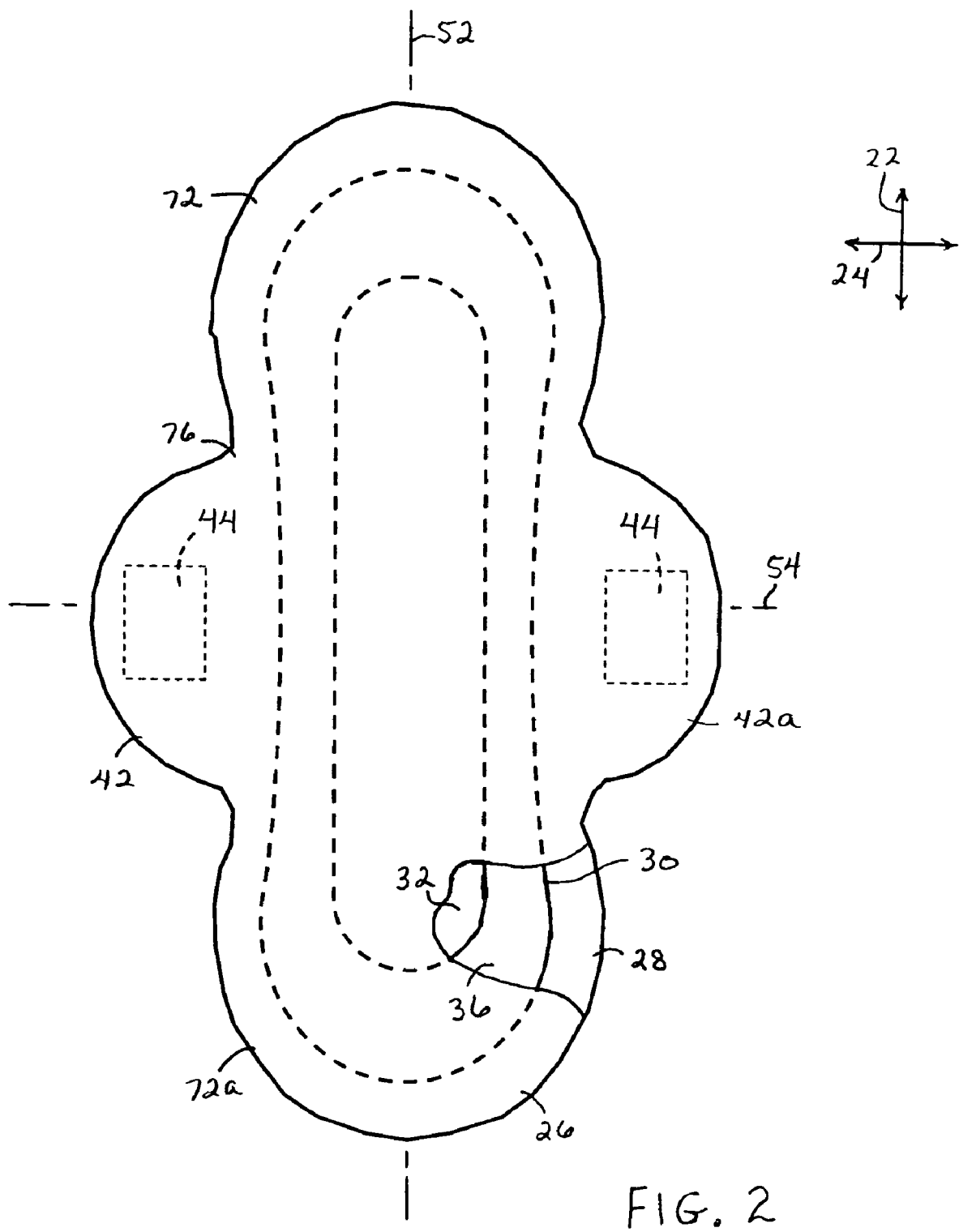
FIG. 2 shows a representative, partially cut-away, top, plan view of a bodyside of an absorbent article having side-panels or wings.
Figure 2A:
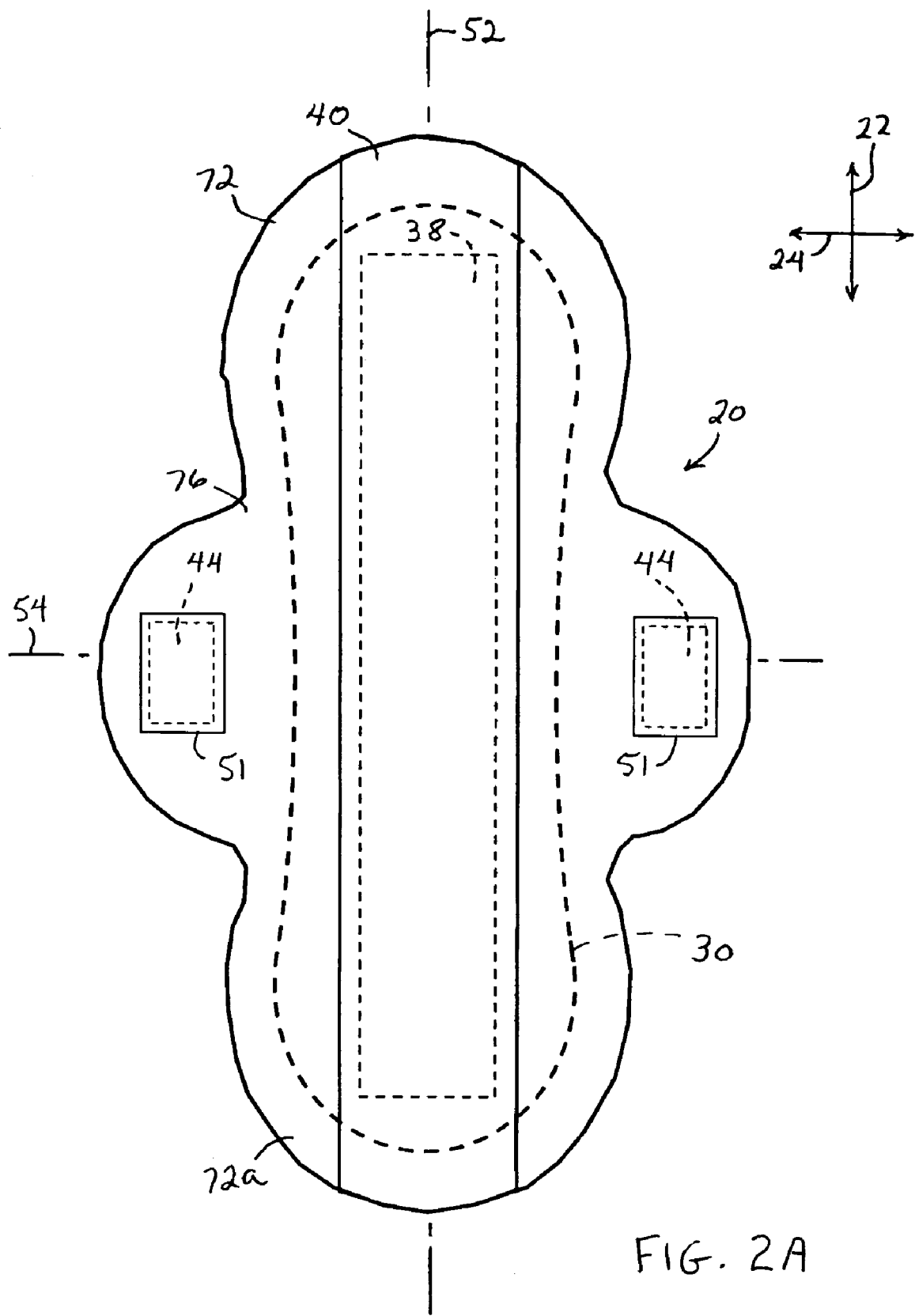
FIG. 2A shows a representative, bottom, plan view of a garment-side of the absorbent article illustrated in FIG. 2.
Figure 2B:
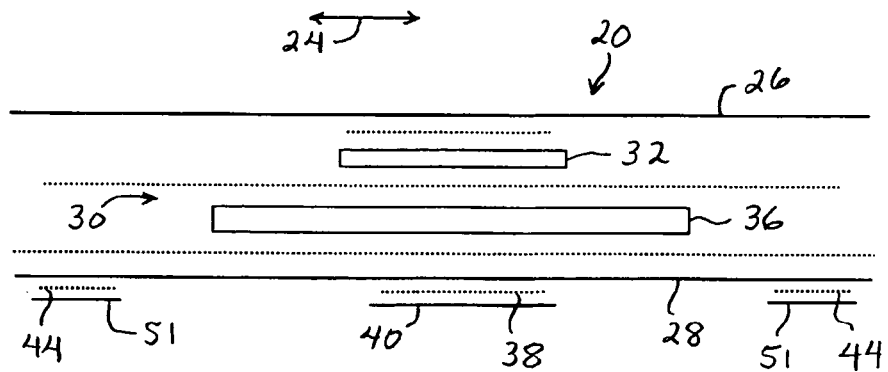
FIG. 2B shows an expanded, schematic view of a representative, transverse cross-section of the absorbent article illustrated in FIG. 2.
Figure 2C:
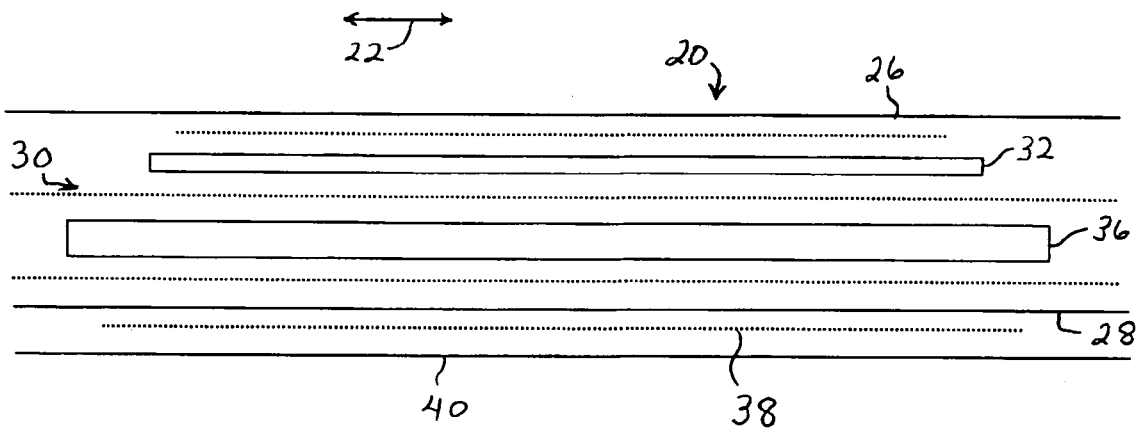
FIG. 2C shows an expanded, schematic view of a representative, longitudinal cross-section of the absorbent article illustrated in FIG. 2.

FIGS. 1 through 2C, illustrate examples of a suitable personal care article 20, such as the representatively shown adult care article, which is configured to incorporate the present invention. The adult care article can, for example, be an adult incontinence product, a feminine care pad or napkin, or the like.

The article 20 can have a longitudinal-direction 22, a relatively shorter, lateral cross-direction 24, and a thickness-direction which extends perpendicular to both the longitudinal-direction and cross-direction. The article also has a first end-section 72, a second end-section 72a, and an intermediate-section 76. Desirably, the intermediate section is contiguous with and interposed between the first end-section 72 and the second end-section 72a. The article includes a liquid permeable topsheet layer 26, and a backsheet layer 28 which is operatively connected to the topsheet layer 26. Optionally, the article may include an absorbent body 30 which is operatively sandwiched between the topsheet and backsheet layers.

With reference to FIGS. 3, 4, 5, 6 and 7, at least a portion of the first end-section 72 has been folded along or otherwise includes a first end-fold-region 58 which is substantially convex along a topsheet-side of the article 20. Additionally, the first end-fold-region 58 is substantially concave along a backsheet-side of the article. At least a portion of the second end-section 72a has been folded along or otherwise includes a second end-fold-region 62 which is substantially convex along the topsheet-side of the article 20. Additionally, the second end-fold-region 62 can be substantially concave along the backsheet-side of the article 20.

In other aspects, the article can include a first, laterally extending, supplemental-fold-region 64, which is positioned between the first end-fold-region 58 and a laterally extending centerline 54 of the article 20. Additionally, a second, laterally extending, supplemental-fold-region 66 can be positioned between the second end-fold-region 62 and the laterally extending centerline 54 of the article 20. The article can also include a garment-attachment mechanism for operatively securing the article to a wearer's undergarment. Further aspects and features are set forth in the present disclosure.

By incorporating its various features and configurations, the article of the invention can better provide desired combinations of small size, discretion, ease of use and comfort. The absorbent articles of the invention can be more discreetly carried in a person's hand, can provide desired levels of liquid intake and retention, and can provide a desired ease of securement to the wearer's undergarment. Where, for example, the article includes a garment-attachment mechanism (e.g. adhesive), the article configurations can help avoid the occurrence of excessive skin irritation from the garment-attachment mechanism, and can help avoid the occurrence of undesired attachments of the garment-attachment mechanism to other portions of the article or to the wearer's body.

In the various configurations of the article 20, the topsheet 26 may include a layer constructed of any operative material, and may be a composite material. For example, the topsheet layer can include a woven fabric, a nonwoven fabric, a polymer film, a film-fabric laminate or the like, as well as combinations thereof. Examples of a nonwoven fabric include spunbond fabric, meltblown fabric, coform fabric, a carded web, a bonded-carded web, a bicomponent spunbond fabric or the like, as well as combinations thereof. For example, the topsheet layer can include a woven fabric, a nonwoven fabric, a polymeric film that has been configured to be operatively liquid-permeable, or the like, as well as combinations thereof. Other examples of suitable materials for constructing the topsheet layer can include rayon, bonded-carded webs of polyester, polypropylene, polyethylene, nylon, or other heat-bondable fibers, polyolefins, such as copolymers of polypropylene and polyethylene, linear low-density polyethylene, aliphatic esters such as polylactic acid, finely perforated film webs, net materials, and the like, as well as combinations thereof.

A more particular example of a suitable topsheet layer material can include a bonded-carded web composed of polypropylene and polyethylene, such as has been used as a topsheet stock for KOTEX brand pantiliners, and has been obtainable from Vliesstoffwerk Christian Heinrich Sandler GmbH & Co. KG, a business having an address at Posffach 1144, D95120 Schwarzenbach/Saale, Germany. Other examples of suitable materials are composite materials of a polymer and a nonwoven fabric material. The composite materials are typically in the form of integral sheets generally formed by the extrusion of a polymer onto a web of spunbond material. In a desired arrangement, the topsheet layer 26 can be configured to be operatively liquid-permeable with regard to the liquids that the article is intended to absorb or otherwise handle. The operative liquid-permeability may, for example be provided by a plurality of pores, perforations, apertures or other openings, as well as combinations thereof, that are present or formed in the topsheet layer. The apertures or other openings can help increase the rate at which bodily liquids can move through the thickness of the topsheet layer and penetrate into the other components of the article (e.g. into the absorbent structure 30). The selected arrangement of liquid-permeability is desirably present at least on an operative portion of the topsheet layer that is appointed for placement on the body-side of the article. The topsheet layer 26 can provide comfort and conformability, and can function to direct bodily exudates away from the body and toward the absorbent structure 30. In a desired feature, the topsheet layer 26 can be configured to retain little or no liquid in its structure, and can be configured to provide a relatively comfortable and non-irritating surface next to the body tissues of a female wearer. The topsheet layer 26 can be constructed of any material which is also easily penetrated by bodily fluids that contact the surface of the topsheet layer.

The topsheet 26 can also have at least a portion of its bodyside surface treated with a surfactant to render the topsheet more hydrophilic. The surfactant can permit arriving bodily liquids to more readily penetrate the topsheet layer.

The surfactant may also diminish the likelihood that the arriving bodily fluids, such as menstrual fluid, will flow off the topsheet layer rather than penetrate through the topsheet layer into other components of the article (e.g. into the absorbent body structure). In a particular configuration, the surfactant can be substantially evenly distributed across at least a portion of the upper, bodyside surface of the topsheet 26 that overlays the upper, bodyside surface of the absorbent.

Where the article includes the absorbent body 30, the topsheet 26 may be maintained in secured relation with the absorbent structure by bonding all or a portion of the adjacent surfaces to one another. A variety of bonding articles known to one of skill in the art may be utilized to achieve any such secured relation. Examples of such articles include, but are not limited to, the application of adhesives in a variety of patterns between the two adjoining surfaces, entangling at least portions of the adjacent surface of the absorbent with portions of the adjacent surface of the topsheet, or fusing at least portions of the adjacent surface of the topsheet to portions of the adjacent surface of the absorbent.

The topsheet 26 typically extends over the upper, bodyside surface of the absorbent structure, but can optionally extend around the article to partially or entirely, surround or enclose the absorbent structure. Alternatively, the topsheet 26 and the backsheet 28 can have peripheral margins which extend outwardly beyond the terminal, peripheral edges of the absorbent structure 30, and the extending margins of the topsheet and backsheet can be joined together to partially or entirely, surround or enclose the absorbent structure.

The backsheet 28 can be operatively connected to the topsheet layer 26 using any suitable technique or any direct or indirect configuration. The connection technique may, for example, include adhesive bonding, thermal bonding, sonic bonding, cohesive bonding, mechanical attachments or the like, as well as combinations thereof. The backsheet layer may include a layer constructed of any operative material, and may or may not have a selected level of liquid-permeability or an operative level of liquid-impermeability, as desired. In a particular configuration, the baffle or backsheet 28 may be configured to provide an operatively liquid-impermeable backsheet structure. The backsheet may, for example, include a polymeric film, a woven fabric, a nonwoven fabric or the like, as well as combinations or composites thereof. For example, the backsheet may include a polymer film laminated to a woven or nonwoven fabric. In a particular feature, the polymer film can be composed of polyethylene, polypropylene, polyester or the like, as well as combinations thereof. Additionally, the polymer film may be micro-embossed, have a printed design, have a printed message to the consumer, and/or may be at least partially colored. Desirably, the backsheet 28 can operatively permit a sufficient passage of air and moisture vapor out of the article, particularly out of an absorbent (e.g. storage or absorbent structure 30) while blocking the passage of bodily liquids. An example of a suitable backsheet material can include a breathable, microporous film, such as a HANJIN Breathable backsheet available from Hanjin Printing, Hanjin P&C Company Limited, a business having offices located in Sahvon-li.Jungan-mvu.Kongiu-City, Chung cheong nam-do, Republic of South Korea. The backsheet material is a breathable film, which is white in color, dimple embossed, and contains: 47.78% calcium carbonate, 2.22% $TiO_2$, and 50% polyethylene.

In a particular feature, the polymer film can have a minimum thickness of no less than about 0.025 mm, and in another feature, the polymer film can have a maximum thickness of no greater than about 0.13 mm. Bicomponent films or other multi-component films can also be used, as well as woven and/or nonwoven fabrics which have been treated to render them operatively liquid-impermeable. Another suitable backsheet material can include a closed cell polyolefin foam. For example, a closed cell polyethylene foam may be employed. Still another example of a backsheet material would be a material that is similar to a polyethylene film which is used on commercially sold KOTEX brand pantiliners, and is obtainable from Pliant Corporation, a business having offices located in Schaumburg, Ill., U.S.A.

The structure of the absorbent body 30 can be operatively configured to provide a desired level of absorbency or storage capacity. More particularly, the absorbent body can be configured to hold a liquid, such as urine, menses, other complex liquid or the like, as well as combinations thereof. As representatively shown, the absorbent body can include a matrix of absorbent fibers and/or absorbent particulate material, and the absorbent fiber can include natural fiber (e.g. woodpulp fluff) and/or synthetic fiber. Additionally, the absorbent body may include one or more components that can modify menses or intermenstrual liquid.

The absorbent structure 30 may also include superabsorbent material. Superabsorbent materials suitable for use in the present invention are known to those skilled in the art, and may be in any operative form, such as particulate form. Generally stated, the superabsorbent material can be a water-swellable, generally water-insoluble, hydrogel-forming polymeric absorbent material, which is capable of absorbing at least about 20, desirably about 30, and possibly about 60 times or more its weight in physiological saline (e.g. saline with 0.9 wt % NaCl). The hydrogel-forming polymeric absorbent material may be formed from organic hydrogel-forming polymeric material, which may include natural material such as agar, pectin, and guar gum; modified natural materials such as carboxymethyl cellulose, carboxyethyl cellulose, and hydroxypropyl cellulose; and synthetic hydrogel-forming polymers. Synthetic hydrogel-forming polymers include, for example, alkali metal salts of polyacrylic acid, polyacrylamides, polyvinyl alcohol, ethylene maleic anhydride copolymers, polyvinyl ethers, polyvinyl morpholinone, polymers and copolymers of vinyl sulfonic acid, polyacrylates, polyacrylamides, polyvinyl pyridine, and the like. Other suitable hydrogel-forming polymers include hydrolyzed acrylonitrile grafted starch, acrylic acid grafted starch, and isobutylene maleic anhydride copolymers and mixtures thereof. The hydrogel-forming polymers are preferably lightly crosslinked to render the material substantially water insoluble. Crosslinking may, for example, be by irradiation or covalent, ionic, Van der Waals, or hydrogen bonding. Suitable materials are available from various commercial vendors such as The Dow Chemical Company and Stockhausen, Inc. The superabsorbent material may desirably be included in an appointed storage or retention portion of the absorbent system, and may optionally be employed in other components or portions of the absorbent article.

The amount of superabsorbent material in the absorbent body 30 can be up to about 75 wt % or more, as determined with respect to the total weight of material in the absorbent body. In particular aspects, the amount of superabsorbent material can be within the range of about 5-35 wt %, and can alternatively be within the range of about 8-20 wt % to provide desired performance. In desired configurations, the amount of superabsorbent can be about 15 wt %.

In particular configurations, the absorbent body 30 can be included in an absorbent article, and can provide a composite, overall absorbent saturation capacity (saturated retention capacity) which is at least a minimum of about 20 grams of 0.9 wt % saline, as determined under substantially unconstrained, free-swell conditions. The overall absorbent capacity can alternatively be at least about 100 grams of 0.9 wt % saline to provide improved performance. In other aspects, the overall absorbent saturation capacity can be up to a maximum of about 500 grams of 0.9 wt % saline or more, and can alternatively be up to about 300 grams of 0.9 wt % saline to provide improved effectiveness. In a desired arrangement, the composite, overall absorbent capacity can be about 150 grams of 0.9 wt % saline.

In other configurations, the absorbent body 30 can be included in a feminine care article, and can provide a composite, overall absorbent saturation capacity which is at least a minimum of about 5.5 grams of menses simulant A. The overall absorbent saturation capacity can alternatively be at least about 40 grams of menses simulant A to provide improved performance. In other aspects, the overall absorbent saturation capacity can be up to a maximum of about 120 grams of menses simulant A, or more, and can alternatively be up to about 88 grams of menses simulant A to provide improved effectiveness. In a desired arrangement, the composite, overall absorbent saturation capacity can be about 60 grams of menses simulant A.

In particular configurations, the absorbent body 30 can be included in a feminine care article, and can provide a composite, overall absorbent retention capacity which is at least a minimum of about 5 grams of menses simulant A. The overall absorbent retention capacity can alternatively at least about 10 grams of menses simulant A to provide improved performance. In other aspects, the overall absorbent retention capacity can be up to a maximum of about 34 grams of menses simulant A, or more, and can alternatively be up to about 20 grams of menses simulant A to provide improved effectiveness. In a desired arrangement, the composite, overall absorbent retention capacity can be about 14.5 grams of menses simulant A.

The menses simulant A is composed of swine blood diluted with swine plasma to provide a hematocrit level of 35% (by volume). A suitable device for determining the hematocrit level is a HEMATOSTAT-2 system, available from Separation Technology, Inc., a business having offices located in Altamonte Springs, Fla., U.S.A. A substantially equivalent system may alternatively be employed. Simulant A is typically used for absorbent capacity tests, where the viscoelastic properties that affect liquid movement have been found to be of little importance.

As representatively shown, the absorbent body 30 of the selected article can comprise a composite structure having a selected plurality of strata or layers. With reference to FIGS. 1 through 2C, for example, the absorbent composite can include an intake layer 32 and an absorbent shaping layer 36, as well as any other desired components, arranged in any operative combination. As representatively shown, the structure of the absorbent body can include an absorbent pad, shaping layer 36 which is positioned between the topsheet 26 and the backsheet 28, and can include an intake layer 32 which is positioned between the topsheet 26 and the shaping layer 36.

In a particular aspect, the article 20 can include a top, bodyside intake layer 32 which is sized and placed to more effectively operate in a target area of the absorbent body 30 where liquids are more likely to be introduced into the article. The material of the intake layer can be configured to provide desired liquid-intake properties, substantially without consideration for delivering shaping properties. For example, the configuration of the intake layer may or may not include properties that are configured to prevent bunching and twisting of the article, particularly the absorbent structure, during ordinary wear.

The intake layer can include material that is configured to quickly absorb and pull liquid away from the body. Accordingly, the intake layer 32 can provide the function of liquid intake and can also provide the functions of liquid distribution, spreading, temporary storage and liquid retention. The intake layer may include natural fibers (e.g. woodpulp fluff), synthetic fibers, superabsorbent materials, a woven fabric; a nonwoven fabric; a wet-laid fibrous web; a substantially unbonded airlaid fibrous web; an operatively bonded, stabilized-airlaid fibrous web; or the like, as well as combinations thereof. Additionally, the absorbent body may include one or more components that can modify menses or intermenstrual liquid.

In a particular arrangement, the intake layer can be a thermally-bonded, stabilized-airlaid fibrous web (e.g. Concert code 175.1020) available from Concert Fabrication, a business having offices located in Gatineaux, Quebec, Canada. The intake layer may optionally be provided by a similar, stabilized airlaid fibrous web available from Buckeye Technologies, Inc., a business having offices located in Memphis, Tenn., U.S.A.

In a desired feature, the intake layer 32 can have a relatively lower basis weight, as compared to the bottom (garment-side) retention/shaping layer 36. Optionally, the basis weight of the intake layer may be equal or similar to the basis weight of the shaping layer. In another feature, the intake layer 32 can have a lower density (e.g., be more lofty), as compared to the retention/shaping layer 36. Alternatively, the basis weight of the intake layer can be higher than or equal to the basis weight of the shaping/retention layer 36.

In a particular aspect, the basis weight of the intake layer 32 can be at least a minimum of about 30 $g/m^2$. The basis weight of the intake layer can alternatively be at least about 100 $g/m^2$, and can optionally be at least about 120 $g/m^2$ to provide improved performance. In other aspects, the basis weight of the intake layer can be up to a maximum of about 250 $g/m^2$, or more. The basis weight of the intake layer can alternatively be up to about 200 $g/m^2$, and can optionally be up to about 175 $g/m^2$ to provide improved effectiveness.

In a desired feature, the top (bodyside) intake layer 32 of the present invention can be smaller in size than the bottom retention/shaping layer 36. Accordingly, the bottom retention/shaping layer 36 can be larger than the top intake layer, and can substantially define the overall size of the absorbent body 30. Optionally, the bottom retention/shaping layer 36 can be substantially equal to, or relatively smaller than the top intake layer.

The intake layer can be substantially centered (in its machine-direction and cross-direction) with respect to the shaping layer. Optionally, the intake layer may be skewed or offset in one direction (e.g. along the machine-direction), depending on where liquid is expected to first enter the absorbent article.

The top intake layer 32 may have any operative shape and/or design. For example, the intake layer may include a single piece of material, or multiple pieces of material. For example, the intake layer may include multiple strips of material. In addition, the intake layer 32 may include holes or apertures to better provide desired liquid-intake properties. The apertures may extend partially or completely through the z-directional thickness of the intake layer 32, as desired.

The shaping layer 36 can provide the functions of liquid storage and retention, liquid distribution, liquid spreading and shape maintenance. The shaping layer may include natural fibers (e.g. woodpulp fluff), synthetic fibers, superabsorbent materials, a Woven fabric; a nonwoven fabric; a wet-laid fibrous web; a substantially unbonded airlaid fibrous web; an operatively bonded, stabilized-airlaid fibrous web; or the like, as well as combinations thereof. Additionally, the shaping layer may include one or more components that can modify the menses or intermenstrual liquid.

In a particular arrangement, the shaping layer can be a thermally-bonded, stabilized-airlaid fibrous web available from Concert Fabrication (Concert code 225.1021), a business having offices located in Gatineaux, Quebec, Canada (e.g. Concert code 225.1021). The shaping layer 36 may optionally be provided by a similar, stabilized airlaid fibrous web available from Buckeye Technologies, Inc., a business having offices located in Memphis, Tenn., U.S.A.

In a particular aspect, the basis weight of the shaping layer 36 can be at least a minimum of about 100 g/m². The shaping layer basis weight can alternatively be at least about 130 g/m², and can optionally be at least about 165 g/m² to provide improved performance. In other aspects, the basis weight of the shaping layer can be up to a maximum of about 400 g/m², or more. The shaping layer basis weight can alternatively be up to about 350 g/m², and can optionally be up to about 325 g/m² to provide improved effectiveness. In a desired configuration, the shaping layer basis weight can be about 225 g/m².

Further details regarding a suitable absorbent and absorbent system are described in U.S. Patent Application Publication 2004/0186448, which was published Sep. 23, 2004. The entire disclosure of this document is incorporated herein by reference in a manner that is consistent herewith.

The personal care article 20 can further include a garment-attachment mechanism operatively connected to a garment-side of the backsheet layer 28. In a desired feature, a selected configuration of a garment-attachment mechanism may be distributed onto the garment-side of the article to help secure the article to the undergarment. Any operative fastening or attachment mechanism may be employed. The garment-attachment may, for example, include an interengaging mechanical fastener, a hook-and-loop fastener, a cohesive fastener, an adhesive fastener or the like, as well as combinations thereof. In particular aspects, the garment-attachment mechanism can include an adhesive 38, and the garment-attachment mechanism can be arranged in any operative configuration, such as the illustrated strip regions. Typically, the garment adhesive can be distributed over the garment-side of the backsheet, and one or more layers or sheets of release material 40 can be removably placed over the garment adhesive during storage, prior to use.

The article 20 can include a system of side-panel or wing portions 42 which can be integrally connected to appointed sections of the side regions along the intermediate portion of the article. For example, the side-panels or wings can be separately provided members that are subsequently attached or otherwise operatively joined to the intermediate portion of the article 20. In other configurations, the wings or side-panels 42 can be unitarily formed with one or more components of the article. As representatively shown in FIGS. 2, 2A and 2B, for example, either or both wing portions may be formed from a corresponding, operative extension of the material employed to form the topsheet 26. Alternatively, either or both wing portions may be formed from a corresponding, operative extension of the material employed to form the backsheet 28, or formed from a corresponding, operative combination of the topsheet and backsheet materials.

Figure 8:
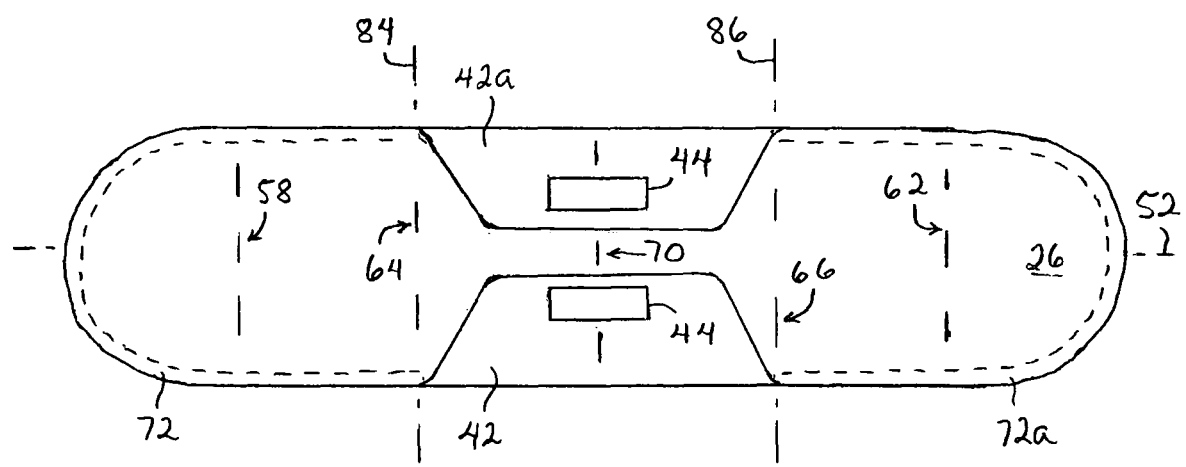
FIG. 8 shows a plan view of a bodyside of a representative article having side-panels or wings arranged in a storage position.

The side-panels can have an appointed storage position (e.g. FIG. 8) in which the side-panels 42 are directed generally inwardly toward the longitudinally-extending centerline 52, in configurations that are well known in the art. The storage position can be configured with the side-panels extending generally adjacent to the garment-side of the backsheet layer 28. Alternatively, the storage position can be configured with the side-panels extending generally adjacent to the bodyside of the topsheet 26. The side-panel that is connected to one side margin may optionally have sufficient cross-directional length to extend and continue past the centerline 52 to approach the laterally opposite side margin of the article. The storage position of the side-panels can ordinarily represent an arrangement observed when the article is first removed from its wrapper or other packaging. Prior to placing the article into a bodyside of an undergarment prior to use, the side-panels 42 can be selectively arranged to extend laterally from the side regions of the article intermediate portion (e.g. FIGS. 2, 2A and 2B). After placing the article in the undergarment, the side-panels 42 can be operatively wrapped and secured around the side edges of the undergarment to help hold the article in place.

The side-panel portions 42 can have any operative construction, and can include a layer of any operative material. Additionally, each side-panel can comprise a composite material. For example, the side-panels may include a spunbond fabric material, a polymer film material, a bi-component spunbond material, a necked spunbond material, a neck-stretched-bonded-laminate (NBL) material, a meltblown fabric material, a bonded carded web, a thermal bonded carded web, a through-air bonded carded web or the like, as well as combinations thereof.

Each side-panel 42 can be joined to its corresponding side region of the article in any operative manner. For example, the side-panel can be joined to the topsheet 26, the backsheet 28 or another article component, as well as any combination thereof. In the illustrated example, each side-panel 42 is joined to the outward, garment-side surface of the backsheet 28, but may optionally be joined to the bodyside surface of the backsheet. The side-panel can be attached with hotmelt adhesive, but any other operative adhesive or attachment mechanism may alternatively be employed.

In another feature, each side-panel portion 42, or any desired combination of the employed side-panel portions, can include a panel-fastener component 50 which is operatively joined to an appointed engagement surface of its associated side-panel. The panel-fastener can be configured to operatively attach to the wearer's undergarment and/or to any appointed, landing-zone portion of the article 20. For example, the panel-fastener can include a system of interengaging mechanical fasteners, a system of adhesive fasteners, a system of cohesive fasteners or the like, as well as combinations thereof.

Either or both side-panels 42 may include a panel-fastener component 44 which includes a hook or other "male" component of an interengaging mechanical fastener system. Any operative hook component may be employed. For example, a suitable hook component material can include a J-hook, mushroom-head hook, flat-top nail-head hook, a palm-tree hook, a multiple-J hook or the like, as well as combinations thereof. Alternatively, either or both side-panels 42 can include a panel-fastener component 44 which alternatively incorporates an operative adhesive. The adhesive may be a solvent-based adhesive, a hotmelt adhesive, a pressure-sensitive adhesive, or the like, as well as combinations thereof. Each section of the adhesive or other fastener-component 44 may be covered with a readily removable release sheet 51.

Further details regarding a suitable panel-fastener system are described in U.S. Patent Application Publication 2004/

0186448, which was published Sep. 23, 2004. The entire disclosure of this document is incorporated herein by reference in a manner that is consistent herewith.

In optional arrangements, the article 20 may include additional components or component layers, as desired. For example, a transfer layer may be positioned between the intake layer 32 and the shaping layer 36. In another feature, the article may include any desired pattern of embossments formed into at least the bodyside surface of the article. The embossing can deform the bodyside of the topsheet and can deform selected portions of the absorbent body 30 to provide operative channel regions that can help block, direct or otherwise control a desired movement of liquids along the bodyside surface of the article. The embossing can also provide an aesthetic benefit to the consumer, and a visual cue regarding fit and leakage protection. In particular arrangements, the embossments can be positioned generally adjacent the perimeter edges of the absorbent body 30. In other aspects, the embossments can be configured to provide a regular or irregular pattern having one or more channels which are distributed in a symmetrical or asymmetrical array, as desired.

With reference to FIGS. 3, 4, 5 and 5A, at least a portion of the first end-section 72 can be folded along or can otherwise include a first end-fold-region 58 which is substantially convex along a topsheet-side of the article 20. Additionally, the first end-fold-region 58 is substantially concave along a backsheet-side of the article. At least a portion of the second end-section 72a has been folded along or otherwise includes a second end-fold-region 62 which is substantially convex along the topsheet-side of the article 20. Additionally, the second end-fold-region 62 can be substantially concave along the backsheet-side of the article 20.

The article 20 can further include a first, laterally extending, supplemental-fold-region 64, which is positioned between the first end-fold-region 58 and a laterally extending centerline 54 of the article 20. Additionally, a second, laterally extending, supplemental-fold-region 66 can be positioned between the second end-fold-region 62 and the laterally extending centerline 54 of the article 20. The first supplemental-fold-region 64 can be substantially convex along a backsheet-side of the article 20, and can be substantially concave along a topsheet-side of the article. Additionally, the second supplemental-fold-region 66 can be substantially convex along the backsheet-side of the article, and can also be substantially concave along the topsheet-side of the article.

As representatively shown, the article 20 may have been folded along or may otherwise include a middle-fold-region 70 which is proximate a laterally extending centerline 54 of the article 20. The configuration of the middle-fold-region can desirably be substantially convex along a backsheet-side of the article 20, and can be substantially concave along a topsheet-side of the article. Alternatively, the configuration of the middle-fold-region 70 may be substantially concave along the backsheet-side of the article 20, and may be substantially convex along the topsheet-side of the article 20.

As representatively shown in FIGS. 3, 4, 5 and 5A, the article 20 may have been folded about a first, laterally extending supplemental-fold-line 84 positioned along a portion of the first end-section 72 which is immediately or otherwise proximally adjacent the intermediate-section 76 of the article 20. The first supplemental-fold-line 84 can be operatively arranged to provide a folded-over first end-section 72 which is positioned relatively onto the intermediate-section 76 of the article 20. Additionally, the article 20 may have been folded about a second, laterally extending supplemental-fold-line 86 positioned along a portion of the second end-section 72a which is immediately or otherwise proximally adjacent the intermediate-section 76 of the article 20. The second supplemental-fold-line 86 can be operatively arranged to provide a folded-over second end-section 72a which is positioned relatively onto the folded-over first end-section 72, thereby providing a preliminary-folded article 82. The preliminary-folded article 82 may also have been folded along a third-laterally extending, composite fold-line 74, thereby providing a composite-folded article 88.

The first, laterally extending supplemental-fold-line 84 can be spaced from a first terminal end-edge 90 of the article 20 by a first spacing distance 78. The first spacing distance can be approximately one-third of an overall longitudinal length 94 of the article 20. Additionally, the second, laterally extending supplemental-fold-line 86 can be spaced from a longitudinally-opposed, second terminal end-edge 92 of the article 20 by a second spacing distance 80 that is approximately one-third of the overall, longitudinal length 94 of the article 20.

Figure 4:
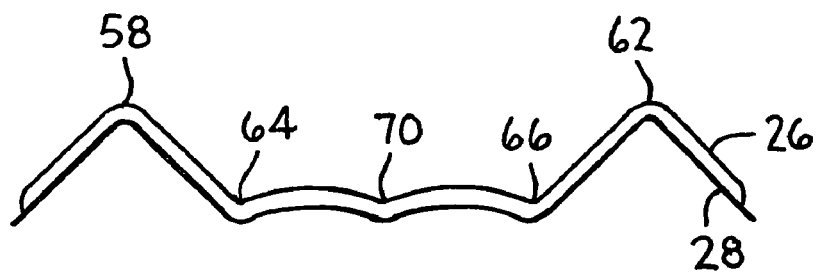
FIG. 4 shows a representative, side elevational view of another absorbent article that has been subjected to a composite folding operation.
Figure 4A:
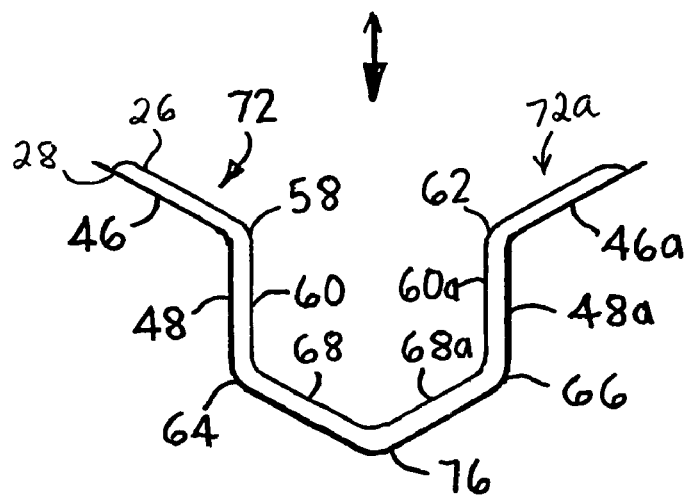
FIG. 4A shows a representative, side elevational view of the absorbent article of FIG. 4 arranged in a transitory position of a composite folding operation.
Figure 4B:
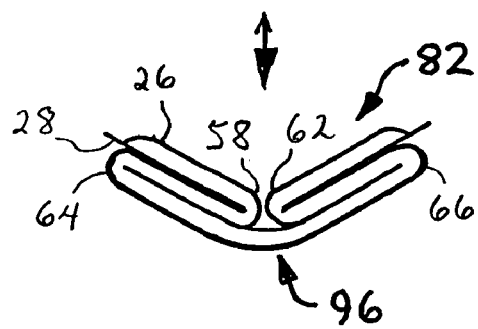
FIG. 4B shows a representative, side elevational view of the absorbent article of FIG. 4 where the article has been folded about a first supplemental-fold-region and a second supplemental-fold-region.

As representatively shown in FIGS. 3B, 3C and 4B, the first end-section 72 can be folded about a first supplemental-fold-line 84 to provide a first supplemental-fold-region 64 which is substantially convex along a backsheet-side of the article 20. Additionally, the first supplemental-fold-region 64 can be substantially concave along a topsheet-side of the article 20. The second end-section 72a can be folded along a second supplemental-fold-line 86 to provide a preliminary-folded article 82. The second supplemental-fold-region 66 can be configured to be substantially convex along a backsheet-side of the article 20. Additionally, the configuration of the second supplemental-fold-region 66 can be substantially concave along a topsheet-side of the article. With reference to FIGS. 3C, 3D, 4B and 4C, the preliminary-folded article 82 can be further folded along the third, laterally extending, composite fold-line 74 to provide a composite fold region 96 which is substantially convex along the backsheet-side of the intermediate section 76 of the article 20.

The first end-section 72 can be folded along the first supplemental-fold-line 84 to provide a first supplemental-fold-region 64 which is substantially convex along a topsheet-side of the article 20. Additionally, the first supplemental-fold-region 64 can be substantially concave along a backsheet-side of the article. The second end-section 72a can be folded along the second supplemental-fold-line 86. The second supplemental-fold-region 66 can be substantially convex along a topsheet-side of the article 20. Additionally, the second supplemental-fold-region 66 can be substantially concave along a backsheet-side of the article. As representatively shown, the first and second folded end sections 72, 72a can cooperatively provide a preliminary-folded article 82. The resulting preliminary-folded article 82 can then be folded along the third, laterally extending, composite fold-line 74 to provide a composite fold-region 96 which is substantially convex along the backsheet-side of the intermediate section 76 of the article 20. Alternatively, the composite fold-region 96 can be substantially concave along the backsheet-side of the article intermediate section 76.

Figure 4C:
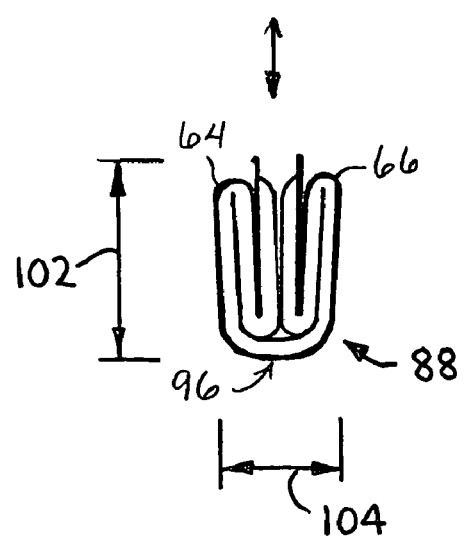
FIG. 4C shows a representative, side elevational view of the absorbent article of FIG. 4 where the article has been folded about a composite-fold-region.
Figure 5:
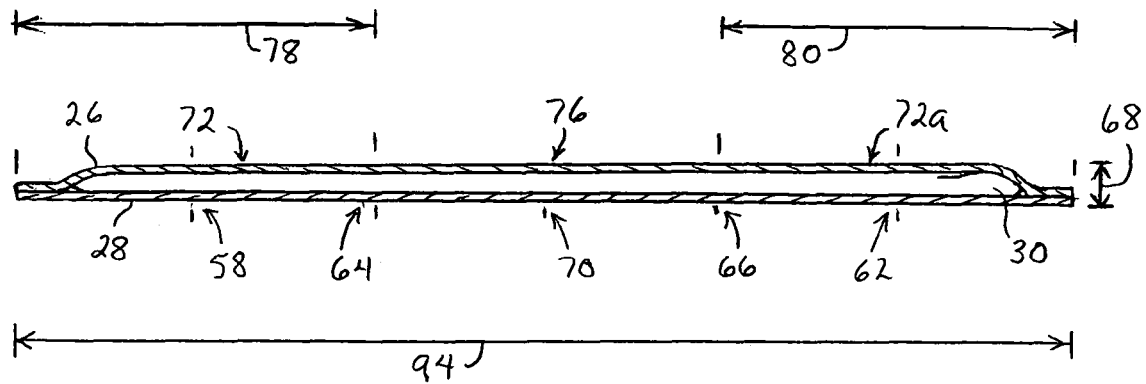
FIG. 5 shows a schematic view of another representative, longitudinal cross-section of an absorbent article.
Figure 5A:
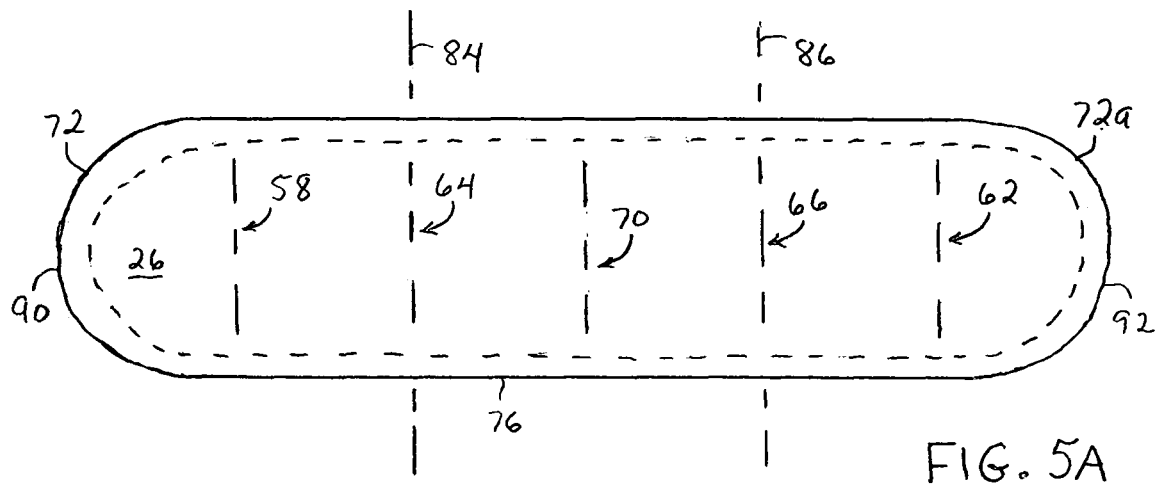
FIG. 5A shows a representative, plan view of a bodyside of the absorbent article illustrated in FIG. 5.
Figure 6:
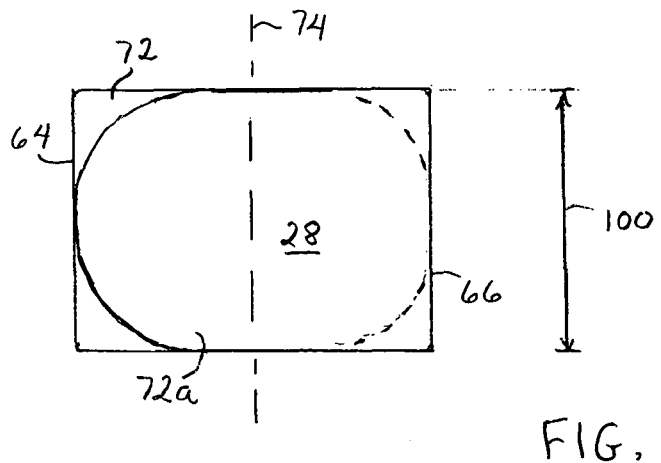
FIG. 6 shows a representative, plan view of a preliminary-folded article.
Figure 7:
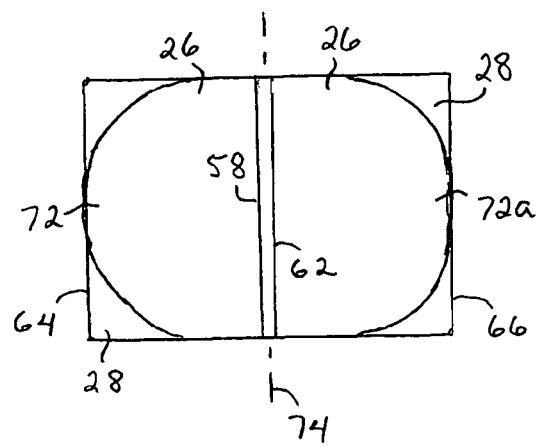
FIG. 7 shows a representative, plan view of another preliminary-folded article.

With reference to FIGS. 3D and 4C, the first and second end-sections 72, 72a can be operatively sandwiched between folded-over sections of the intermediate portion 76 of the article 20. In a particular aspect, the article 20 can be folded along a third, laterally extending, composite fold-line 74 which is operatively arranged to approximately bisect the preliminary-folded article 82. In another aspect, the first supplemental fold-line 84 and the second supplemental-fold-line 86 can be configured to approximately trisect the overall longitudinal length 94 of the article 20.

As representatively shown in FIGS. 3 through 3D, a first, topsheet portion in the folded-over first end-section 72 can be positioned onto an intermediate topsheet portion in the intermediate-section 76 of the article 20. Additionally, a second-topsheet portion in the folded-over second end-section 72a can be positioned onto a first, backsheet portion in the folded-over first end section 72.

In an optional arrangement representatively illustrated in FIGS. 4 through 4C, the first end-fold-region 58 can be configured to place or otherwise position a first longitudinally-outboard region 46 of the backsheet 28 in the first end-section 72 at a location which is operatively adjacent a second longitudinally-inboard region 48 of the backsheet 28 in the first end-section 72. Similarly, the second end-fold-region 62 can be configured to place or otherwise position a second longitudinally-outboard region 46a of the backsheet 28 in the second end-section 72a at a location which is operatively adjacent a second longitudinally-inboard region 48a of the backsheet 28 in the second end-section 72a. In addition, the first supplemental-fold-region 64 can be configured to place or otherwise position a longitudinally-inboard region 60 of the topsheet 26 in the first end-section 72 at a location which is operatively adjacent a first region 68 of the topsheet in the intermediate section 76. Similarly, the second supplemental-fold-region 66 can be configured to place or otherwise position a longitudinally-inboard region 60a of the topsheet 26 in the second end-section 72a at a location which is operatively adjacent a second region 68a of the topsheet in the intermediate section of the article.

In a desired aspect, the article 20 can be folded along the third, composite fold-line 74 in a configuration which positions an intermediate backsheet portion in the intermediate-section 76 of the article 20 along an outward-facing, substantially convex side of the composite fold-region 96 (e.g. FIGS. 3D and 4C). In a particular arrangement, for example, the composite fold-region 96 can include a cooperative combination of the first end-fold-region 58, the second end-fold-region 62 and the middle-fold-region 70 (e.g. FIG. 3D).

Where the article 20 includes at least a pair of laterally extending and laterally opposed side-panel or wing portions 42, 42a. The wing portions 42 can be arranged in a storage position, with the wing portions located adjacent a selected, outer surface of the article 20, and extending inboard towards the longitudinal centerline 52. As representatively shown in FIG. 7, for example, the wing portions 42 can be configured to be substantially, immediately adjacent the topsheet-side of the article. Optionally, the wing portions 42 can be configured to be substantially, immediately adjacent the backsheet-side of the article.

Desirably, the folding of the article end sections (72, 72a) along the respective supplemental fold-lines (84, 86) can be conducted after placing the wings portions 42, 42a in their storage positions. The folding of the article end sections may optionally be conducted prior to placing the wings portions in their storage positions. The absorbent article 20 may have a configuration in which two, three or more laterally-extending fold-lines and fold-regions are positioned to extend through each individual wing portion. In a particular aspect, the absorbent article 20 can have a configuration in which not more than one laterally-extending fold-line or fold-region is positioned to extend through each individual wing portion.

The article 20 can also be configured to have a selected article length 94 and a selected article thickness 68, as determined when the article is in its flat-out condition with substantially all gathering folding removed, (e.g. FIGS. 5 and 5A) to help provide desired benefits. In a particular aspect, the article length can be not more than a maximum of about 325 mm. The article length can alternatively be not more than about 300 mm, and can optionally be not more than about 240 mm. In further aspect, the article thickness can be not more than a maximum of about 7 mm, as determined under a restraining pressure of 0.1 psi (0.7 KPa). The article thickness can alternatively be not more than about 5 mm, and can optionally be not more than about 2.5 mm. When the article length and thickness are within the desired values, the article can provide improved discretion and comfort.

The composite-folded article 88 can have a selected length 100, a selected width 102 and a selected thickness 104. The composite-folded thickness is determined under a restraining pressure of 0.1 psi (0.7 KPa). In a particular aspect, the composite-folded length 100 can be less than 10 cm to provide desired levels of discretion. The composite-folded length can alternatively be less than 7 cm, and can optionally be less than 4 cm to provide desired benefits. In another aspect, the composite-folded width and thickness have been configured to provide a selected girth, which extends around the composite-folded article and along the width and thickness dimensions of the composite-folded article. In desired arrangements, the composite-folded girth can be less than about 15 cm. The girth can alternatively be less than 10 cm, and can optionally be less than about 5 cm to provide improved benefits. In a particular arrangement, the composite-folded girth can be less than about 15 cm and the composite-folded length can be less than about 10 cm. Another arrangement of the composite-folded article can have a girth that is less than about 10 cm and a length that is less than about 7 cm. In a further arrangement, the girth can be less than about 5 cm and the length can be less than about 4 cm.

The selected length and girth dimensions of the composite-folded article 88 can help provide improved discretion and convenience. By incorporating the length and girth dimensions, the composite-folded article can be more discreetly hidden in a user's hand, and can be more discreetly carried and transported.

Figure 9:
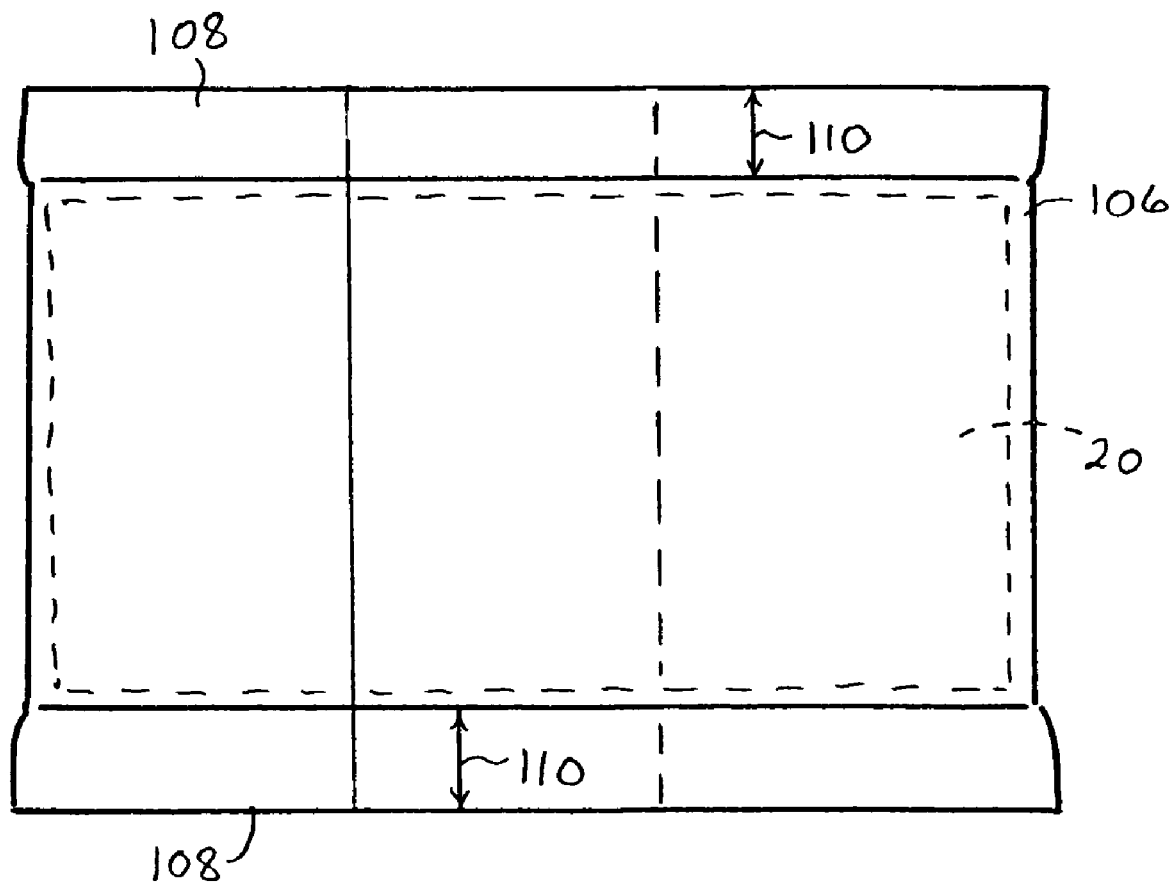
FIG. 9 shows a representative arrangement of an absorbent article contained in a pouch or wrapper member.

With reference to FIGS. 9 and 9A, the personal care article 20 can further include a pouch member 106 or other wrapper member which can operatively enclose at least a major portion or an otherwise significant portion of the personal care article 20 in its folded condition (e.g. a composite-folded article 88).

The pouch can have a system of one or more pouch seams, such as the illustrated pair of opposed side-seams 108. Each pouch seam can have a distinctively small width dimension 110. In a particular aspect, the width of the pouch seam width can be not more than a maximum of about 2 cm. The pouch seam width 110 can alternatively be not more than about 1 cm, and can optionally be not more than about 0.5 cm.

The selected width of a side seam of the pouch can help provide improved discretion and convenience. By incorporating the width, the pouch that contains the composite-folded article 88 can be more discreetly hidden in a user's hand, and can be more discreetly carried and transported.

Those skilled in the art will recognize that the present invention is capable of many modifications and variations without departing from the scope thereof. Accordingly, the detailed description and examples set forth above are meant to be illustrative only and are not intended to limit, in any manner, the scope of the invention as set forth in the appended claims.

The invention claimed is:

1. A composite-folded article comprising
   a personal care article having a longitudinal-direction; a relatively shorter lateral cross-direction, a first end-section; a second end-section; and an intermediate-section which is interposed between said first end-section and said second end-section; said personal, care article comprising:

a liquid permeable topsheet layer, and a backsheet layer operatively connected to the topsheet layer;

wherein the personal care article has been folded about a first, laterally extending supplemental-fold-line positioned along a portion of the first end-section which is proximally adjacent the intermediate-section of the personal care article, the first supplemental-fold-line operatively arranged to provide a folded-over first end-section which is positioned onto the intermediate-section;

the personal care article has been folded about a second, laterally extending supplemental-fold-line positioned along a portion of the second end-section which is proximally adjacent the intermediate-section of the personal care article, the second supplemental-fold-line operatively arranged to provide a folded-over second end-section which is positioned onto the folded-over first end-section, thereby providing a preliminary-folded article; and the preliminary-folded article has been folded along a third, laterally extending, composite fold-line, thereby providing the composite-folded article; and the personal-care article further includes a garment-attachment mechanism operatively connected to a garment side of the backsheet layer.

2. A composite-folded article as recited in claim 1, wherein the first, laterally extending supplemental-fold-line is spaced from a first terminal end edge of the personal care article by a first spacing distance that is approximately one-third of an overall, longitudinal length of the personal care article; and the second, laterally extending supplemental-fold-line is spaced from a longitudinally-opposed, second terminal end edge of the personal care article by a second spacing distance that is approximately one-third of the overall, longitudinal length of the personal care article.

3. A composite-folded article as recited in claim 1, wherein said first end-section has been folded about a first supplemental-fold-line to provide a first supplemental-fold-region which is substantially convex along a backsheet-side of the personal care article;

said second end-section has been folded along a second supplemental-fold-line to provide a second supplemental-fold-region which is substantially convex along a backsheet-side of the personal care article; and the preliminary-folded article has been folded along said third, laterally extending, composite fold-line to provide a composite fold region which is substantially convex along the backsheet-side of the intermediate section of the personal care article.

4. A composite-folded article as recited in claim 1, wherein the article further includes a pair of laterally extending and laterally opposed wing portions;

said first end-section has been folded along the first supplemental-fold-line to provide a first supplemental-fold-region which is substantially convex along a topsheet-side of the personal care article;

said second end-section has been folded along the second fold-line to provide a second supplemental-fold-region which is substantially convex along a topsheet-side of the personal care article;

the wing portions have been arranged in a storage position which is adjacent a selected outer surface of the personal care article;

the preliminary-folded article has been folded along said third, laterally extending, composite fold-line to provide a composite fold region which is substantially convex along the backsheet-side of the of the intermediate section of the personal care article; and which not more than one laterally-extending fold-line or fold-region has been positioned to extend through each individual wing portion.

5. A composite-folded article as recited in claim 1, wherein the first and second end sections of the personal care article are operatively sandwiched between folded-over sections of the intermediate-section of the personal care article.

6. A composite-folded article as recited in claim 1, wherein the personal-care article has been folded along a third, laterally extending, composite fold-line which is operatively arranged to approximately bisect the preliminary-folded article.

7. A composite-folded article as recited in claim 1, further including an absorbent body operatively held between the topsheet layer and backsheet layer.

8. A composite-folded article as recited in claim 1, wherein a first, topsheet portion in the folded-over first end-section has been positioned onto an intermediate topsheet portion in the intermediate-section of the personal care article.

9. A composite-folded article as recited in claim 1, wherein a second, topsheet portion in the folded-over second end-section has been positioned onto a first, backsheet portion in the folded-over first end-section.

10. A composite-folded article as recited in claim 1, wherein the personal care article has been folded along the third, composite fold-line in a configuration which positions an intermediate backsheet portion in the intermediate-section of the personal care article along an outward-facing, substantially convex side of the composite fold-region.

11. A composite-folded article as recited in claim 1, wherein the first fold-line and the second fold-line have been configured to approximately trisect a longitudinal length of the personal care article.

12. A composite-folded article as recited in claim 1, wherein the composite-folded article has included a girth which is less than about 15 cm.

13. A composite-folded article as recited in claim 1, wherein the composite-folded article has included a composite-folded girth which is less than about 15 cm and a composite-folded length which is less than about 10 cm.

* * * * *